(12) United States Patent
Huettman

(10) Patent No.: US 6,671,043 B1
(45) Date of Patent: Dec. 30, 2003

(54) PROCESS AND APPARATUS FOR MEASURING DENSITY FLUCTUATIONS OCCURRING WITH PULSED IRRADIATION OF A MATERIAL

(75) Inventor: Gereon Huettman, Luebeck (DE)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 181 days.

(21) Appl. No.: 09/614,701

(22) Filed: Jul. 12, 2000

(30) Foreign Application Priority Data

Jul. 12, 1999  (DE) .......................... 199 32 477

(51) Int. Cl.[7] .............. G01J 3/00; G01J 5/02; A61B 18/18
(52) U.S. Cl. .................. 356/300; 356/43; 356/51; 356/342; 250/341.1; 250/341.6; 250/341.8; 606/4; 606/9; 606/10; 606/11; 606/12
(58) Field of Search ............. 606/2, 4–6, 8–12, 606/27, 31, 127, 128; 356/43, 300, 335–343, 51; 250/226, 336.1, 340, 341.1, 341.6, 341.8, 342–346; 374/100; 600/310; 128/898

(56) References Cited

U.S. PATENT DOCUMENTS

| | | | | | |
|---|---|---|---|---|---|
| 3,700,890 | A | * | 10/1972 | Kruezer | 250/43.5 |
| 4,236,827 | A | * | 12/1980 | Horiba et al. | 356/437 |
| 4,682,897 | A | * | 7/1987 | Saito et al. | 374/45 |
| 6,018,391 | A | * | 1/2000 | Yoshida | 356/349 |
| 6,285,894 | B1 | * | 9/2001 | Oppelt et al. | 600/322 |

OTHER PUBLICATIONS

R. M. Measures "Laser Remote Sensing," Fundamentals and Applications, John Wiley &Sons, Inc., 1984.*

* cited by examiner

Primary Examiner—Linda C. M. Dvorak
Assistant Examiner—Ahmed Farah
(74) Attorney, Agent, or Firm—Crowell & Moring LLP

(57) ABSTRACT

A process and an apparatus preferably used during the photocagulation of the fundus of human eyes or animals measures density fluctuations caused by pulsed irradiation, such as a laser irradiation source, on a material. A wherein a measuring signal is acoustically or optically detected. The change of the intensity and/or of the time slope of the measuring signal resulting from the irradiation of a specific material point is detected. A linear thermo-elastic signal fraction is removed from the measuring signal.

5 Claims, 4 Drawing Sheets

PROCESS AND APPARATUS FOR MEASURING DENSITY FLUCTUATIONS OCCURRING WITH PULSED IRRADIATION OF A MATERIAL

BACKGROUND OF THE INVENTION

This application claims the priority of German Application 199 32 477.8, filed Jul. 12, 1999, the disclosures of which are expressly incorporated by reference herein.

The present invention relates to a process and an apparatus for measuring density fluctuations caused by pulsed irradiation on a material, particularly biological tissue, in the case of which a measuring signal is acoustically or optically detected, particularly for an apparatus for the photocoagulation of specific points on the ocular fundus and here particularly of pigmented tissue.

It is known to cause changes in a targeted manner on the surface or in the interior of materials by the irradiation of the materials, particularly by laser irradiation. In material processing or in the medical field, this results in a therapeutically effective irradiation of tissue. Corresponding processes and apparatuses are described, for example, in DE 44 00 674 C2; DE 39 35 528 A1 DE 43 00 378 A1 U.S. Pat. No. 4,543,486; A. Tam: "Applications of Photoacoustic Sensing Techniques", Rev. Mod. Phys., Vol. 58, 381–431 (1986); C. P. Lin, M. W. Kelly: "Cavitations and Acoustic Emission around Laser-Heated Microparticles", Appl. Phys. Lett., Vol 72, 1–3 (1998); and A. A. Oraevsky, S. L. Jacques, F. K. Tittel: "Measurement of Tissue Optical Properties by Time-Resolved Detection of Laser-Induced Transient Stress", Appl. Optics, Vol. 36, 402–415 (1997).

It is known therefrom to carry out a differentiation of materials by the detection of the mechanical shock waves and acoustic pulses generated during the irradiation step. In the known processes and apparatuses, information concerning characteristics of the material, such as the absorption, the thermal coefficient of expansion and the ablation threshold can be obtained by the opto-acoustic effect.

SUMMARY OF THE INVENTION

An object of the present invention is to detect a change of the material caused specifically by the irradiation.

This object has been achieved according to the present invention by providing that at least one of a change of intensity and time slope of a measuring signal occurring during the irradiation of a specific material point, and removing a linear thermo-elastic signal fraction from the measuring signal, by providing that the analyzing device has a separating device operable to separate a thermo-elastic signal fraction from the measuring signal, a measuring device operable to detect intensity and time slope of the measuring signal freed of a thermo-elastic signal fraction, and a detector device operable to detect a change of at least one of the intensity and the time slope of the measuring signal. Furthermore, a use of the apparatus is taught for measuring changes at one or several specific points of a biological tissue, particularly on the fundus of the eye during the irradiation. In addition, the present invention provides an apparatus for the phototherapy, e.g., photocoagulation, of specific points on the ocular fundus, particularly of pigmented tissue.

The acoustic or optical signal caused by the specific change of the material as a result of the irradiation is separated from the thermo-elastic signal which contains only information concerning characteristics of the material. The thermo-elastic signal increases approximately linearly with the applied energy or power, without any change of the time slope of the curve. The change of the material caused specifically by the irradiation results in a change of the intensity and/or of the time slope of the measuring signal.

As a result of the present invention, a control of the influencing or changing of the material by way of the irradiation can be advantageously achieved therefrom by evaluating the acoustically or optically obtained measuring signals, which, in addition to the thermo-elastic expansion, are generated by occurrences, such as chemical reactions, ablation, phase transitions, plasma formation, etc. In addition, the detection of occurrences can also be achieved in the interior of the material to be processed, particularly biological tissue on the fundus of the eye, which is often not optically accessible.

An exact dosimetry of the irradiation is achieved by the present invention with respect to the energy, the power, the time slope and the spatial distribution for achieving the desired effect. This is required particularly in the medical field in the case of a therapeutically effective irradiation of biological tissue. Mainly, with the present invention, an individual dosimetry can be achieved before or during the irradiation, which is necessary particularly in the field of medicine because of the variation of the characteristics of tissue. Such an individual dosimetry for regulating and controlling the laser parameters is desirable, for example, during the coagulation of the ocular fundus. This will be explained in detail in the following by way means of the example of the selective coagulation of the retinal pigment epithelium (RPE).

A number of diseases of the eye can be treated by a coagulation of the RPE. The RPE is a single-cell layer of highly pigmented cells which is situated between the photoreceptors and the vessels to be supplied. Although the strong absorption of the RPE permits a selective depositing of the light energy in this cell layer, as a result of the heat conduction, adjoining cell layers (such as photoreceptors), which do not contribute to a therapeutic success, may also be damaged during the photocoagulation. The propagation of the heat can be prevented by using brief laser exposures. This limits thermal damages of the photocoagulation to the RPE and prevents a loss of vision, so that a selective coagulation of the RPE becomes possible. For increasing the therapeutic range of the selective photocoagulation, multiple pulses are used. Currently, pulse series of 500 pulses with a pulse length of 3 $\mu$s are used in clinical studies.

As a function of the apportionment of the laser irradiation, the temperature on the surface of the absorbing melanin granules may become so high that locally there is an evaporation of water and the formation of rapidly expanding gas bubbles which may also destroy cells and tissue. This mechanism is also capable of destroying pigmented cells with few side effects if the pulse energy is situated close to the energy threshold for the bubble formation. These two mechanisms, specifically thermal damages as a result of the denaturing of important biomolecules and thermomechanical damages by bubble formation, which play a varying role at different pulse lengths and pulse numbers, can therefore be used for a selective destruction of the RPE.

For controlling the mechanism and the range of the damage, a dosimetry is advantageous with respect to the pulse energy. Since the transparency of the optical media of the eye and the pigmentation of the RPE varies considerably from one patient to the next, an avoidance of damages to the photoreceptors is permitted as a result of the invention. In contrast to the conventional coagulation, the selective effects on the RPE are not directly visible for the physician because of their spatial boundaries. An advantageous simple non-invasive procedure therefore controls the laser during the coagulation, or previously determines the required laser pulse energy by a test coagulation in the critical range.

BRIEF DESCRIPTION OF THE DRAWINGS

Other objects, advantages and novel features of the present invention will become apparent from the following detailed description of the invention when considered in conjunction with the accompanying drawings wherein.

DETAILED DESCRIPTION OF THE DRAWINGS

Figure 1:
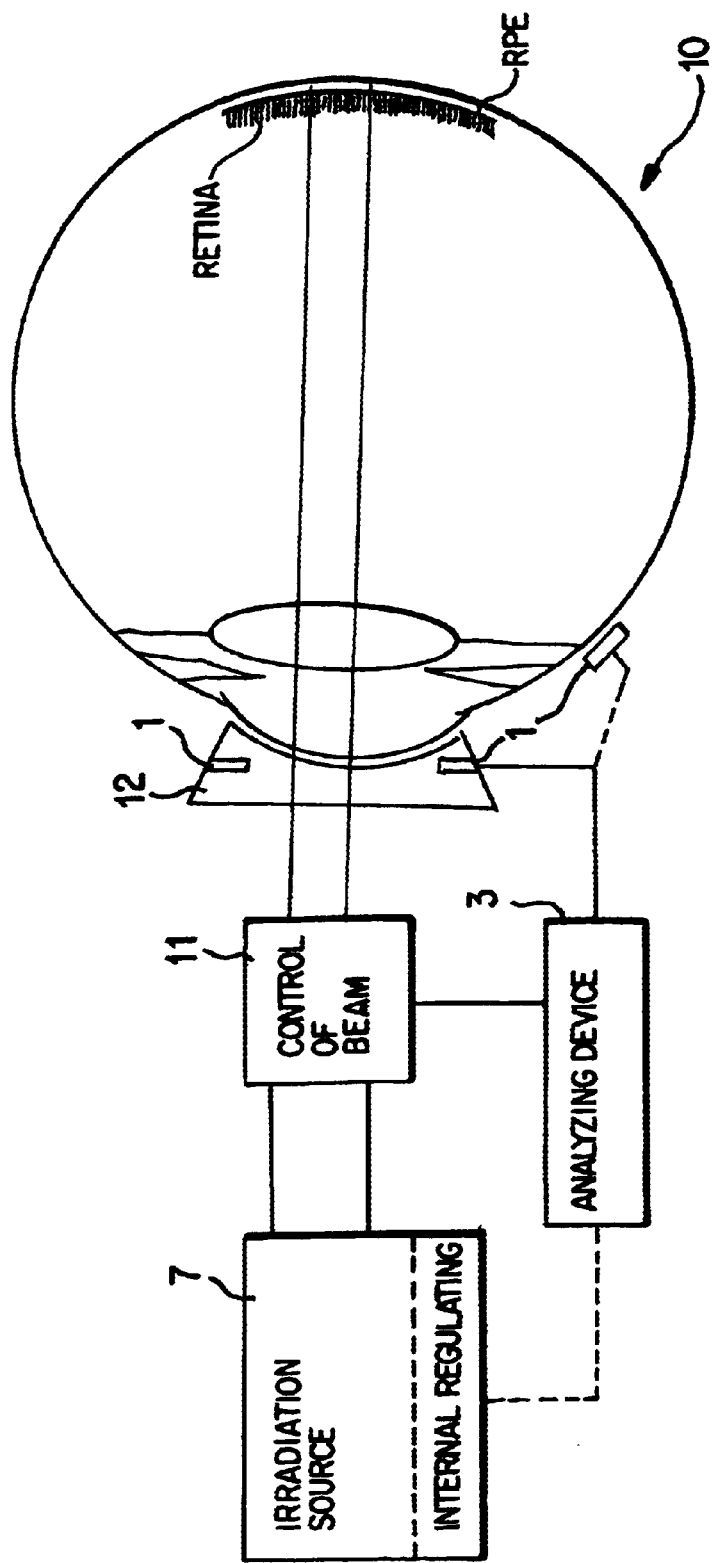
FIG. 1 is a schematic view of a first embodiment of the apparatus of the present invention.
Figure 2:
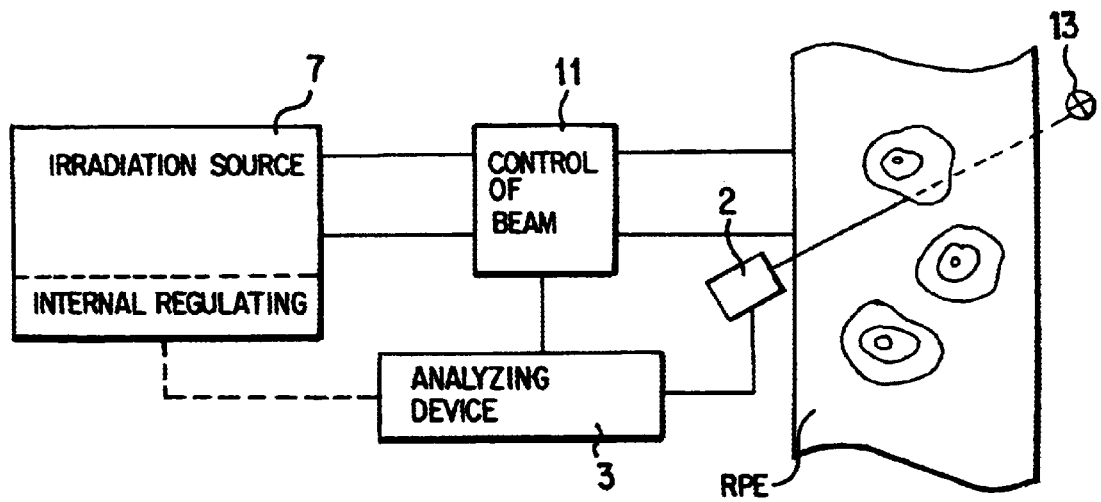
FIG. 2 is a schematic view of a second embodiment of the apparatus of the present invention.

FIGS. 1 and 2 each illustrate an apparatus for the photocoagulation of retinal pigment epithelial cells (RPE cells). The photocoagulation is carried out by a laser beam which is supplied by a laser beam source 7. The pulse energy of the laser beam is set by an apportioning device 11 which is controlled by the output signal of an analyzing device 3. The setting of the pulse energy of the laser beam can also take place, however, by the direct control of the laser beam source 7, as indicated by the dash lines in FIGS. 1 and 2.

The analyzing device 3 is connected to a measuring transducer which, in FIG. 1, is constructed such that it can be acoustically coupled and, in FIG. 2, is constructed such that it can be optically coupled. In the embodiment of FIG. 1, the acoustic coupling takes place by way of the ball of an eye 10 on whose RPE cells the photocoagulation is carried out. For this purpose, the measuring transducer 1 can be placed directly on the eyeball or, for example, as a ring-shaped measuring transducer 1, can be placed on the eye by way of a contact lens 12.

In the embodiment of FIG. 2, the density fluctuations on the RPE cells caused as a result of the treatment of material during the irradiation are detected by the optically coupled measuring transducer 2 by changes of the reflections at the boundary surfaces by reflection, diffraction or refraction on the density fluctuations or by changes of the optical paths. As far as measuring techniques are concerned, this can be implemented, for example, by an interferometer, by measuring the running time or by imaging processes which show phase contrasts, such as dark-field processes, schlieren processes, or the like. Optionally, an additional light source 13 may also be provided. The measuring transducer 1 or 2 supplies a signal which is proportional to the density fluctuations and can be electrically analyzed. For this purpose, the measuring transducer 1 or 2 is connected to the analyzing device 3.

Figure 3:
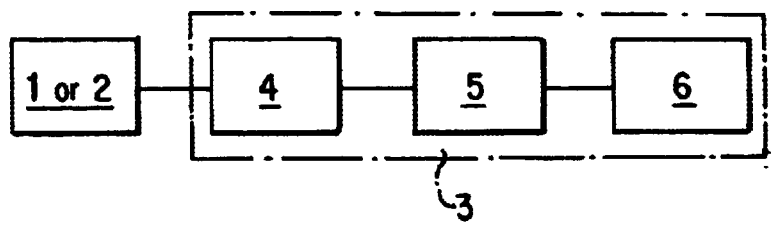
FIG. 3 is a schematic view of an analyzing device which is used in the embodiments of FIGS. 1 and 2.

As illustrated in FIG. 3, the analyzing device 3 contains a separating device 4 which removes the thermo-elastic signal fraction, which increases linearly with the energy or power applied by the irradiation, from the electric signal supplied by the measuring transducer 1 or 2. The time slope of the curve is, however, not changed in this case. The measuring signal freed of the thermo-elastic fraction is detected by a measuring device 5 and is transmitted to a detector device 6. The detector device 6 detects a change of the intensity and of the time slope of the measuring signal. As a function thereof, the dose of the irradiation source, and here particularly the pulse energy of the pulsed irradiation, can be set either by the apportioning device 11 or directly by the internal apportioning of the irradiation source 7.

For optimizing the signal emitted by the measuring transducer, the analyzing device may, for example, have an amplifier stage, a filter or an impedance transformer. This configuration improves the sensitivity and the signal-to-noise ratio. The analyzing device 3 can be implemented by programmed or otherwise logically controlled electronic devices, such as semiconductor devices, which are further developed in a user-specific manner.

Figure 4:
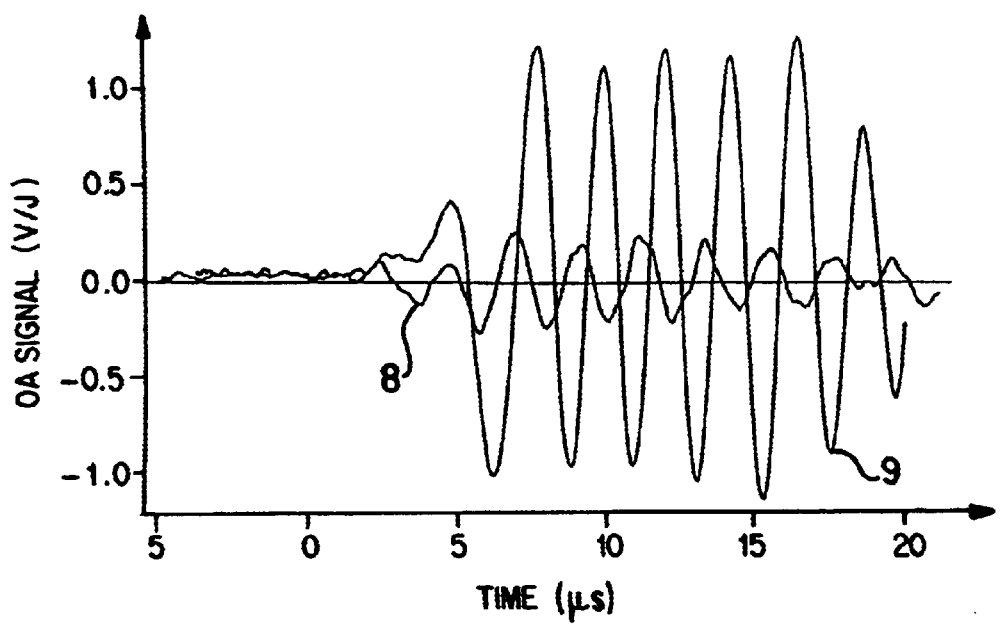
FIG. 4 is a graph showing measuring signals scaled to the pulse energy of the irradiation.

FIG. 4 illustrates the acoustic signals measured during the laser irradiation of the RPE. Curve 8 is the signal scaled to the pulse energy during an irradiation during which the cells of the RPE are not damaged. At higher laser pulse energies, the shape and size of the scaled signal (curve 9) will change. This is connected with damage to the cells. In this case, the cell death and the change of the acoustic signal were caused by evaporation and bubble formation. The cell death, which may be a desirable therapeutic effect, depending on the laser parameters, occurs either together with a change of the acoustic or optically detected signal or at a defined lower or higher pulse energy. By solving the heat conduction equation, the temperature and, when the dependency of the cell damage and tissue damage on the temperature and the time is known, the damage can be predicted also for higher or lower pulse energies.

For example, during the irradiation of RPE-cells, it was observed that, when individual pulses are used, damage to the cells occurred at the pulse parameters (such as pulse energy, pulse length), at which the shape and the size of the scaled signal changed. In the case of an irradiation with pulse trains of, for example, 10 to 10,000 pulses, damage was observed already at pulse energies which were lower than those at which the signal changes occurred but were in a fixed relationship with the latter. This relationship could be predicted by calculations of the temperature in the cells during the irradiation and the knowledge of the damage mechanism.

The present invention therefore permits a control and regulation of laser parameters for achieving a desired therapeutic effect also in cases in which other processes cannot be used or can be used only at high technical expenditures.

Figure 5A:
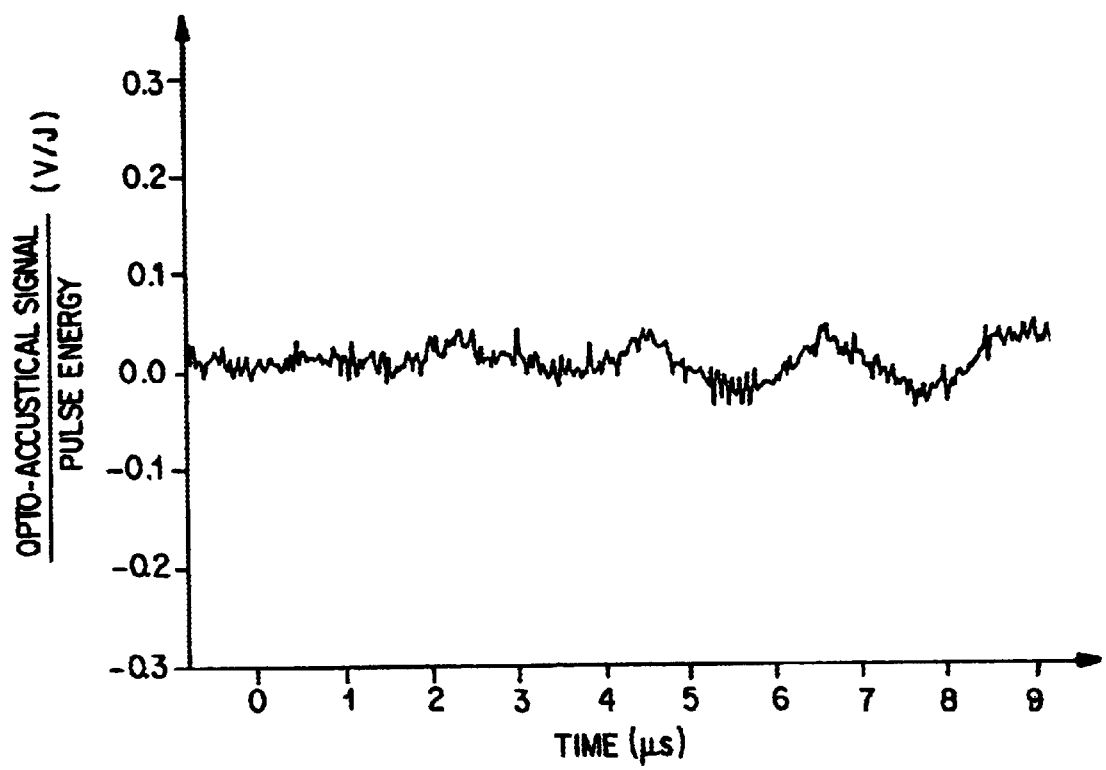
FIG. 5 is a view of graphs (A), (B) and (C) showing various scaled measuring signals during the irradiation of retinal pigment epithelial cells.
Figure 5B:
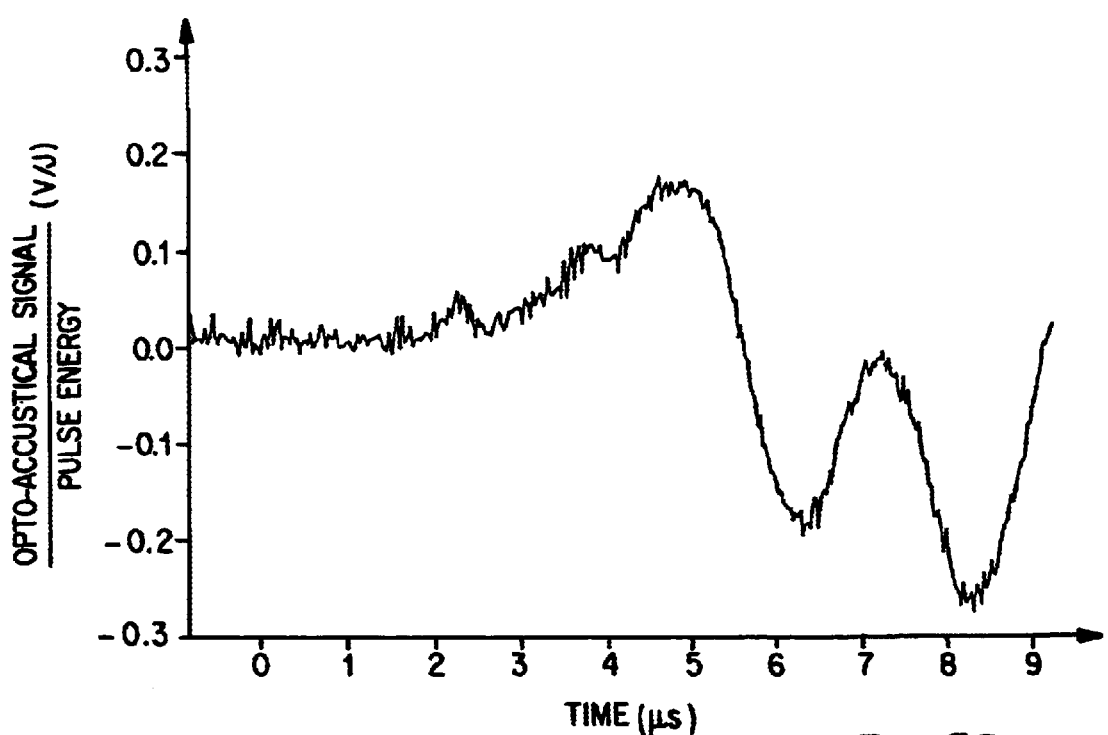
Figure 5C:
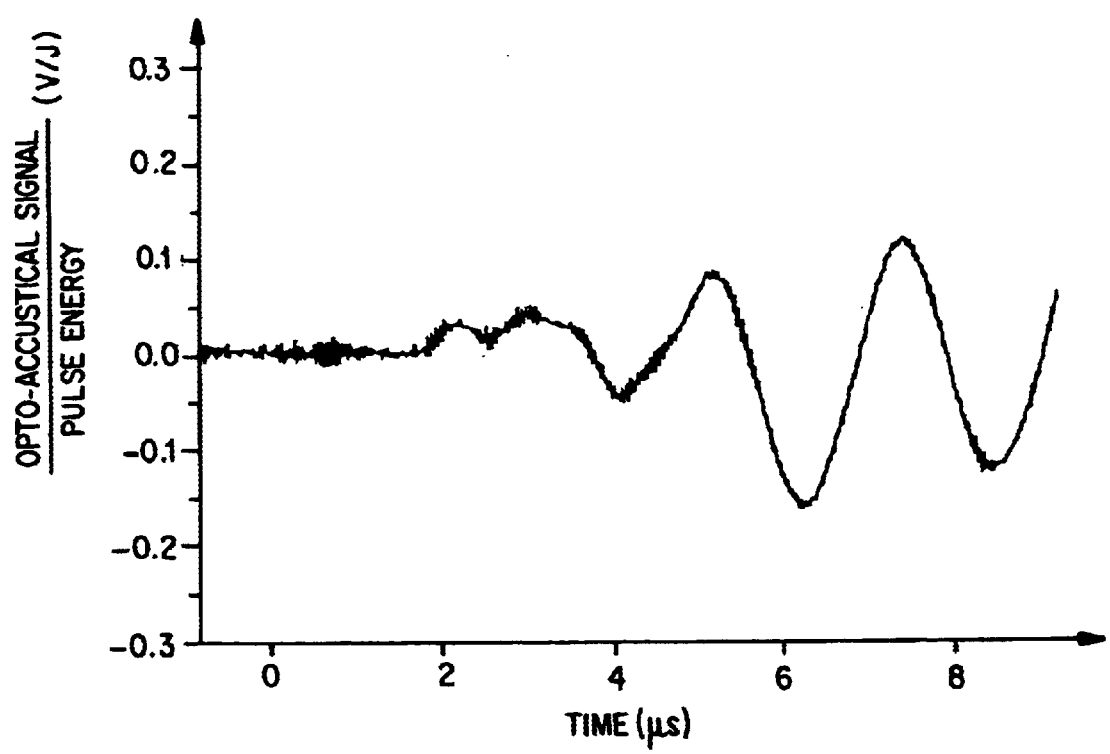

FIG. 5 illustrates in views (A), (B) and (c) various measuring signals which were received as scaled acoustic signals at different doses of the pulse energy during the irradiation of RPE cells. The quotient of the opto-acoustic signal and the pulse energy is shown in $V/(J/cm^2)$ on the ordinate, and the time is shown in us on the abscissa. The change of the respective acoustic signal shows the formation of gas bubbles by explosive evaporation during the laser irradiation of the RPE cells.

The present invention therefore shows a process and an apparatus, particularly for controlling and regulating the primary irradiation effect, for example, during the irradiation of pigmented tissue by pulsed light irradiation. The measurement of the sound emission or optical changes which is or are caused by the desired irradiation effect can be correlated with a dose effect relationship. Particularly in the case of an inhomogeneous deposition of the materials energy, such as tissue with absorbing components, the specific sound emission or optical change connected with a change of material is utilized for controlling or regulating the effect.

In this case, the change emitting the sound or the optical change may either be the desired effect or, in the sense of a dose effect relationship, may be correlated with the effect, so that it is possible to determine the required dose by test exposures. In particular, non-linear phenomena, such as evaporation or plasma formation, which are caused by the irradiation in the irradiated medium, can be utilized as the source of the acoustic and optical signals. The acoustic signal can be detected, for example, by a contact microphone or an optical process. The dosimetry during the irradiation of pigmented tissue, particularly of the fundus of the eye, represents an embodiment.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

List of Reference Numbers

1 Measuring transducer which can be acoustically coupled
2 measuring transducer which can be optically coupled
3 analyzing device
4 separating device for separating a thermo-elastic signal fraction from the measuring signal
5 measuring device
6 detector device
7 irradiation source
8 scaled measuring signal without change of the material
9 scaled measuring signal with a change of the material, particularly cell damage on biological tissue
10 eye
11 apportioning device
12 contact lens
13 light source

What is claimed is:

1. Process for measuring density fluctuations caused by pulsed irradiation on a material, comprising detecting a measuring signal acoustically or optically, wherein at least one of a change of intensity and time slope of the measuring signal occurring during the irradiation of a specific material point is detected, removing a linear thermo-elastic signal fraction from the measuring signal, and setting an irradiation dose as a function of at least one of the change of intensity and the time slope of the measuring signal except for the removed fraction.

2. Process according to claim 1, wherein the irradiation is laser radiation.

3. Process according to claim 1, wherein one of pulse energy and pulse length is set.

4. Process according to claim 1, wherein the irradiation dose comprising pulse energy is set close to an energy threshold triggering a material change or a phase transition.

5. Apparatus for measuring density fluctuations caused by a pulsed irradiation source on a material, comprising a measuring transducer configured to be acoustically coupled to the irradiated material and to supply an electrically analyzable measuring signal, and an analyzing device operatively connected to the measuring transducer, wherein the analyzing device has a separating device operable to separate a linearly increasing thermo-elastic signal fraction from the measuring signal, a measuring device operable to detect intensity and time slope of the measuring signal freed of the linearly increasing thermo-elastic signal fraction, and a detector device operable to detect a change of at least one of the intensity and the time slope of the measuring signal wherein said pulsed irradiation source is operable to be set to a specific pulse energy as a function of at least one of the change of the intensity and of the time slope of the measuring signal except for the separated fraction.

* * * * *